United States Patent
Ripoll et al.

(10) Patent No.: US 7,226,623 B2
(45) Date of Patent: Jun. 5, 2007

(54) **IN VITRO AND IN VIVO ANTI-INFLAMMATORY EFFECTS OF A SESQUITERPENE LACTONE EXTRACT FROM CHICORY (*CICHORIUM INTYBUS* L.)**

(75) Inventors: Christophe Ripoll, Saint-Andre (FR); Barbara Schmidt, Somerset, NJ (US); Nebojsa Ilic, Highland Park, NJ (US); Ilya Raskin, Manalapan, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 11/262,676

(22) Filed: Oct. 31, 2005

(65) Prior Publication Data

US 2007/0098827 A1 May 3, 2007

(51) Int. Cl.
*A61K 36/00* (2006.01)
(52) U.S. Cl. .................................. 424/725
(58) Field of Classification Search .............. None
See application file for complete search history.

(56) References Cited

U.S. PATENT DOCUMENTS 6,645,534 B2 * 11/2003 Hermand .................. 424/773

2004/0208944 A1 * 10/2004 Malone et al. .............. 424/764

OTHER PUBLICATIONS

1997. Peters et al. A study on the effects of sample pre-treatment on the amount of sesquiterpene lactones found in chicory (*Cichorium intybus* L.) by ELISA and HPLC. Z Lebensm Unters A. 204, pp. 189-193.*

* cited by examiner

*Primary Examiner*—Christopher R. Tate
*Assistant Examiner*—Melenie McCormick
(74) *Attorney, Agent, or Firm*—Mathews, Shepherd, McKay & Bruneau, P.A.

(57) ABSTRACT

A method of preparing a chicory extract enriched with sesquiterpene lactones is provided. The method includes performing an initial extraction chicory in a polar solvent, such as methanol or ethanol, at ambient temperature to form an alcoholic extract. The alcoholic extract is subsequently defatted with a non-polar solvent, preferably hexane or n-heptane. A second extraction of the defatted alcoholic extract is performed with a solvent which is more polar than the solvent used in the defatting process and less polar than the solvent used in the initial extraction, for example, it can be chosen from the group consisting of ethyl acetate, n-butanol, isopropanol, n-propanol, dichloromethane, acetonitrile, and mixtures thereof; resulting in a sesquiterpene lactones enriched extract, preferably containing at least 60% sesquiterpene lactones.

18 Claims, 2 Drawing Sheets

IN VITRO AND IN VIVO ANTI-INFLAMMATORY EFFECTS OF A SESQUITERPENE LACTONE EXTRACT FROM CHICORY (CICHORIUM INTYBUS L.)

BACKGROUND OF THE INVENTION

1. Field of the Invention

The present invention relates to chicory extracts. More specifically, the present invention relates to methods of extracting sesquiterpene lactones from chicory.

2. Description of Related Art

Chicory (Cichorium intybus L.) is a perennial herb native to Europe, North Africa, and Western Asia and naturalized in North America. There are many commercial uses of the plant, leading to the development of several distinct cultivars. Chicory roots are dried and roasted and used as a coffee substitute. Young and tender roots can also be boiled and eaten. The chicons (shoots and leaves) are grown for consumption in salads and vegetable dishes. Chicory extracts can be added to alcoholic and non-alcoholic beverages.

Besides its alimentary use, chicory also has a history of medicinal use. Chicory roots have been used as a digestive aid, diuretic, laxative and mild sedative. Hepatoprotective agents have been described in the seeds. Chicory is recognized as a good source of dietary fibers such as inulin and fructo-oligosaccharides, which have health-promoting properties. Its aqueous, ethanolic, and methanolic extracts have been shown to affect cholesterol uptake and tumor development in mice, prevent immunotoxicity induced by ethanol, and have anti-inflammatory proprieties in vitro and in vivo. Studies have linked sesquiterpene lactones, the bitter agents in chicory, to some of the anti-inflammatory health benefits. Sesquiterpene lactones are $C_{15}$ terpenoid compounds that have a range of biological and pharmaceutical activities. They have been reported as the active compounds of some well-known medicinal plants, such as Arnica montana (leopard's bane) and Tanacetum parthenium (feverfew) and have been used clinically for migraines and arthritis. Studies have shown that sesquiterpene lactones inhibit pro-inflammatory gene expression through inactivation of the transcription factor nuclear factor-κB (NF-κB). Several pro-inflammatory genes, including those coding for cyclooxygenase-2 (COX-2), tumor necrosis factor-alpha (TNF-α), inducible nitric oxide synthase (iNOS), and interleukin 1, beta (Il1β) contain a binding site in their promoter region for NF-κB and therefore their expression can be mediated through the NF-κB pathway.

Inflammation plays an important role in the development of various diseases such as cancer, rheumatoid arthritis and arteriosclerosis. Inflammatory diseases are currently treated with steroidal and nonsteroidal anti-inflammatory drugs (NSAIDs). Unfortunately, both of these widely-prescribed drug classes have significant negative side effects, reducing their use in certain segments of the population. There is a need to develop new drugs with novel modes of action that do not produce considerable side effects. The uses of plant extracts as anti-inflammatory therapeutics are widely reported and can provide safe, efficacious, and cost-effective alternatives to synthetic drugs.

For example, a pharmaceutical composition containing chicory extract can be used to treat inflammatory and auto-immune diseases including but not limited to rheumatoid arthritis, asthma, inflammatory bowel disease, Crohn's disease, multiple sclerosis, psoriasis and skin rushes, chronic obstructive pulmonary disease, allergic rhinitis, cardiovascular disease, lupus, and metabolic syndrome.

SUMMARY OF THE INVENTION

A method of preparing a chicory extract enriched with sesquiterpene lactones is provided. The method includes performing an initial extraction of chicory in a polar solvent, such as methanol or ethanol. This first extraction can be performed at a range of temperatures but does not need to be at temperatures above or below ambient temperature. In one embodiment the first extraction is performed for a period of about 24 hours.

This extract is subsequently defatted with a non-polar solvent, preferably hexane or n-heptane. An additional extraction of the defatted extract is performed with a third solvent. The third solvent is preferably chosen from the group consisting of ethyl acetate, n-butanol, dichloromethane, acetonitrile, and mixtures thereof. The resulting extract is enriched with sesquiterpene lactones. In the preferred embodiment, the extract contains at least 60% sesquiterpene lactones.

The method of preparing a chicory extract can also include the step of removing the solvents from the extract. Alternatively, the extract can be subjected to counter-current chromatography.

Pharmaceutical compositions comprising the chicory extract, as described above, and one or more pharmaceutically acceptable formulation agents are also encompassed by this invention. Nutraceutical compositions comprising the chicory extract, as described above, and one or more nutraceutical acceptable formulation agents are also encompassed by this invention.

Another aspect of the present invention provides a functional food product. The functional food product includes functional food ingredients and the chicory extract. Another aspect of the present invention provides for a cosmetic product comprising the chicory extract, as described above, and one or more cosmetic ingredients.

In one embodiment, the pharmaceutical composition, nutraceutical, functional food or cosmetic composition, as described above, comprise an effective amount of the chicory extract to treat inflammatory and autoimmune diseases or to prevent and treat conditions associated with inflammation, such as skin aging, for example.

In another aspect of the invention, the sesquiterpene-enriched chicory extract is used to treat and reduce inflammation.

The invention will be more fully described by reference to the following figures.

DETAILED DESCRIPTION

Figure 1:
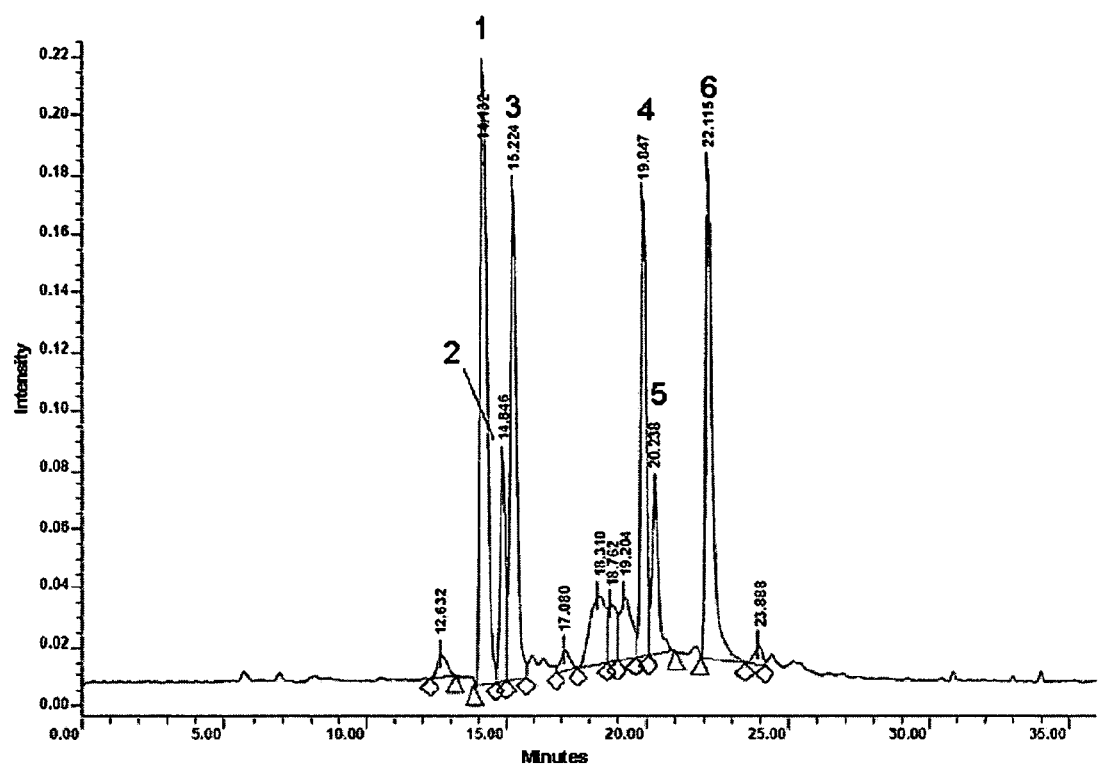
FIG. 1 LC-MS chromatogram of chicory extract showing putative compounds; 1: dihydrolactucin; 2: lactucin; 3: (4-OH-phenyl) acetate ethyl-ester; 4: 8-deoxylactucin; 5: (epi) jacquinelin; 6: dihydrolactucipicrin.

Reference will now be made in greater detail to a preferred embodiment of the invention, an example of which is illustrated in the accompanying drawings. Wherever possible, the same reference numerals will be used throughout the drawings and the description to refer to the same or like parts.

The present invention relates to a chicory extract prepared by the steps of performing an initial extraction in a polar solvent to form an extract, defatting the extract with a non-polar solvent, and performing a second extraction of the defatted extract with a third solvent resulting in an extract containing sesquiterpene lactones. Subsequently, the solvents can be removed form the extract. A pharmaceutical composition, nutraceutical, functional food or cosmetic product containing the extract can be obtained by admixing or processing the extract with suitable excipients, carriers or other ingredients.

Suitable polar solvents include all straight chain and branched primary alcohols and chemical derivatives thereof, provided that the additional chemical groups do not destroy the polarity of the fluid or increase the polarity of the fluid to the level of water, which is expressly excluded from the definition of a polar fluid. Preferred polar fluids are liquids, such as the lower molecular weight, straight chain, primary alcohols, such as ethanol or methanol. Suitable polar solvents also include a mixture of water and a polar fluid such as ethanol. For example, a polar solvent can be 70%-90% alcohol. The resulting extract can be defatted under suitable defatting process conditions in a non-polar solvent. Example non-polar solvents can include petroleum, ether, pentane, n-heptane, hexane or mixtures thereof. The secondary extraction of the defatted extract is performed with an aprotic polar or protic polar solvent which is more polar than the non-polar solvent used in the defatting process and is less polar than the solvent used in the first extraction step. The solvent used in the secondary extraction is typically immiscible with the solvent used in the initial extraction. Suitable solvents include n-butanol, isopropanol, n-propanol, dichloromethane, acetonitrile, ethyl acetate or mixtures thereof.

The first and second extractions can be performed for a period of time that results in an extract containing at least 60% sesquiterpene lactones at ambient temperature.

Large scale production can be accomplished using this procedure with counter-current chromatography methods to obtain large amounts of an extract rich in sesquiterpene lactones. Counter-current chromatography is a liquid-liquid separation technique using a long rotating coiled tube to partition compounds in two immiscible solvents. Various sizes and types of tubes may be used with different conditions known to those skilled in the art as a way of defatting the initial polar extract and isolating sesquiterpene lactones. Various modes of administration, including all modes known in the art, are contemplated for use in delivering the chicory extract to a mammal such as a human patient. Preferred modes of administration of the plant, e.g., chicory extract, include parental (e.g., intravenous, intramuscular and subcutaneous), oral administration, and topical administration. The chicory extract can be added to a pharmaceutical composition, nutraceutical, functional food and/or cosmetic composition in any suitable amount. In an embodiment, the pharmaceutical composition, nutraceutical, functional food and/or cosmetic composition includes the chicory extract of the present invention in an amount of at least 0.5% by weight, preferably from about 1% to about 80% by weight, more preferably about 1% to about 20% by weight.

In an embodiment, the pharmaceutical compositions containing the extract of the present invention may be in any form suitable for oral use, such as e.g., tablets, troches, lozenges, aqueous or oily suspensions, dispersible powders or granules, emulsions, hard or soft capsules, or syrups or elixirs. Compositions intended for oral use can be prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient(s) in admixture with non-toxic pharmaceutically acceptable excipients, such as inert diluents, granulating, disintegrating and lubricating agents, which are suitable for the manufacture of tablets. The tablets may be uncoated or they may be coated by known techniques to delay disintegration and absorption in the gastrointestinal tract and thereby provide a sustained action over a longer period. Formulations for oral use may also be presented as hard gelatin capsules wherein the active ingredient is mixed with an inert solid diluent, or as soft gelatin capsules wherein the active ingredients is mixed with water or an oil medium. Aqueous suspensions contain the active material in admixture with excipients suitable for the manufacture of aqueous suspensions, such as e.g., suspending agents, dispersing or wetting agents, preservatives, coloring agents, flavoring agents, and sweetening agents. Dispersible powders and granules suitable for preparation of an aqueous suspension by the addition of water provide the active ingredient(s) in admixture with a dispersing or wetting agent, suspending agent and one or more preservatives. Additional excipients, for example sweetening, flavoring and coloring agents, may also be present.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

Administration of the chicory extract of the present invention can also be used for treating inflammation or autoimmune diseases in a mammal, including a human, comprising administering an effective amount of a composition of the chicory extract of the present invention, including, but not limited to rheumatoid arthritis, asthma, inflammatory bowel disease, Crohn's disease, multiple sclerosis, psoriasis and skin rushes, chronic obstructive pulmonary disease, allergic rhinitis, cardiovascular disease, lupus, and metabolic syndrome.

Although the present invention is further described in the examples below, the scope of the present invention is not limited to that described in these examples.

EXAMPLE 1

Extraction Procedure

Chicory cv. Sacson roots were commercially obtained. The sesquiterpene-enriched extract of the present invention was prepared by the following procedure. Dry, milled chicory roots (1 kg) were extracted in 10 L of 95% ethanol for 24 hours at room temperature (24° C.). The resulting ethanolic extract was defatted with n-heptane. A secondary extraction of the defatted ethanolic extract with ethyl acetate created an extract containing at least 60% sesquiterpene lactones as determined by LC-MS. Solvents were removed under vacuum, creating a brown syrup that was stored at 4° C.

EXAMPLE 2

LC-MS Analysis

Chicory extract was separated and analyzed with the Waters (Milford, Mass.) LC-MS Integrity™ system consisting of a solvent delivery system including a W616 pump and W600S controller, W717 plus auto-sampler, W996 PDA detector and Waters TMD Thermabeam™ electron impact (EI) single quadruple mass detector. Data were collected and analyzed with the Waters Millennium® v. 3.2 software, linked with the 6$^{th}$ edition of the Wiley Registry of Mass Spectral Data, containing 229,119 EI spectra of 200,500 compounds. Substances were separated on a Phenomenex® Luna C-8 reverse phase column, size 150×2 mm, particle size 3 µm, pore size 100 Å, equipped with a Phenomenex® SecurityGuard™ pre-column. The mobile phase consisted of 2 components: Solvent A (0.5% ACS grade acetic acid in double distilled de-ionized water, pH 3-3.5), and Solvent B (100% Acetonitrile). The mobile phase flow was adjusted at 0.25 ml/min, and generally a gradient mode was used for all analyses. The gradient points were for time 0.0 minutes—95% A and 5% B; for time 25.0 minutes—5% A and 95% B; held isocratic for 2 minutes and from 27.0 minutes to 30.0 minutes back to initial conditions of 95% A and 5% B. A column equilibration time of 15 minutes was set between subsequent injections.

LC-MS Analysis

The major peaks shown in the LC-MS chromatogram (FIG. 1) matched the UV spectra and fragmentation patterns of several known sesquiterpene lactones. Putative compounds included dihydrolactucin, 14.1 min; lactucin, 14.8 min; a (4-OH-phenyl) acetate ethyl-ester compound, 15.2 min; 8-deoxylactucin, 19.8 min; (epi-)jacquinelin, 20.2 min; and dihydrolactucopicrin at 22.1 min. Several of the major peaks were isolated and tested in the in vitro assays (data not shown); however, no single compound had the activity greater than the whole extract.

The inventors have conducted a number of experimental tests to demonstrate the beneficial effects of the present invention.

EXAMPLE 3

Cell Culture

RAW 264.7 murine monocyte/macrophages (ATCC TIB-71) were maintained in Dulbecco's Modified Eagle Medium (D-MEM) supplemented with 10% fetal bovine serum (FBS) and 1% streptomycin and were kept in a humidified 37° C. incubator with 5% $CO_2$. Cells were subcultured by scraping when plates reached 90% confluency with a 1:5 ratio.

Quantitative Real-Time RT-PCR

Murine RAW macrophages 264.7 were plated in 24-well plates 12 hours prior to treatment. The cells were treated with extracts of various concentrations for 2 hours before elicitation with lipopolysaccharide (LPS) at 1 µg/ml. After 6 hours of treatment, RNA was extracted from cells using TRIzol® reagent (Invitrogen, Carlsbad, Calif.) according to the manufacturer instructions. RNAs were quantified spectrophotometrically at 260 nm and stored at −80° C. until real-time PCR could be performed.

RNA was treated with Dnase RQ1 (Promega, Madision, Wis.) before performing reverse transcription with superscript II H-(Invitrogen, Carslad, Calif.) according to the manufacturer instructions. The cDNAs obtained were then amplified by real-time PCR. Expression of COX-2, iNOS, TNF-α, IL1β and β-actin gene expression levels was quantified using a Stratagene Mx 3000P™ Real-Time PCR System (Stratagene, La Jolla, Calif.). Primers for each gene were designed using Primer Express® vers. 2.0 software (Applied Biosystems, Foster City, Calif.; Table 1). Real-time PCR analyses were carried out using a Brilliant® SYBR® Green PCR master mix kit (Stratagene) according to kit instructions. Samples were amplified using the following program: 2 minutes incubation at 50° C.; initial denaturation and polymerase activation at 95° C. for 10 minutes; 40 PCR cycles consisting of 15 seconds at 95° C. and 60 seconds at 60° C. each. The RNA expression was analyzed by ΔΔCt methods using β-Actin gene as normalizer. Amplification of specific transcripts was further confirmed by obtaining melting curve profiles. All samples were run in duplicate; five independent analyses were performed.

EXAMPLE 4

Griess Assay for NO Production

Down-regulation of various pro-inflammatory genes, including iNOS, IL1β and TNF-α, can reduce nitric oxide production by macrophages. In order to confirm that changes in pro-inflammatory gene expression were affecting cellular function, the Griess assay was performed to indirectly measure nitric oxide production by LPS-induced macrophages by measuring nitrite. For the assay, RAW cells were plated in a 96-well plate at a minimum density of $5\times10^3$ cells/well and grown for 24 hours. Cells were stimulated with 1 µg/mL LPS with simultaneous addition of chicory extract (10-100 µg/mL), aspirin (10 mM), or vehicle control (0.5% DMSO). After 24 hours, conditioned media (50 µl) was removed and immediately mixed with 100 µl of Griess reagent (10% sulfanilamide, 1% naphthalene-ethylenediamine dihydrochloride in 5% $H_3PO_4$). After incubation for 15 minutes at room temperature, the samples were read at 550 nm using a microplate spectrophotometer (Molecular Devices, Sunnyvale, Calif.). Data for each treatment were normalized based on results from an MTT cell proliferation assay.

EXAMPLE 5

MTT Cell Proliferation Assay

The MTT (3-(4,5-dimethylthiazol-2-yl)-2,5-diphenyl-tetrazolium bromide, Sigma, St. Louis, Mo.) tetrazolium dye assay was performed to measure cell viability after 24 hours of incubation with treatments. MTT (100 µg/mL) was added to the media of each well and plates were incubated for 3 hours. After 3 hours, media was removed and dimethylsulfoxide (DMSO, 200 µL) was added to each well to solubilize purple formazan crystals created by mitochondrial dehydrogenase reduction of MTT. After 5 minutes of additional incubation, absorbance was read at 550 nm on a microplate spectrophotometer (Molecular Devices, Sunnyvale, Calif.).

EXAMPLE 6

Carrageenan-Induced Rat Paw Edema

Groups of 5 adult male and female Wistar rats with body weights from 136 g to 170 g were used for this study. Rats were housed five animals per cage in a room kept at 24-26° C. and fed ad libitium. Before the experiment began, rat paw sizes were recorded by measuring paw volume three times on each animal using a plethysmometer (Ugo Basile, Comerio VA, Italy). The values were averaged to give a baseline paw size value. To start the experiment, animals were given a subcutaneous injection of 1% carrageenan (100 µl; Sigma, St. Louis, Mo.) in the area of the back paw to induce an acute inflammatory reaction (paw edema). One hour after carrageenan injection, rats were orally gavaged with chicory extract or vehicle control (4% apricot kernel balm). Paw size was measured at 3 hours, 5 hours, and 24 hours after injection. The increase in paw edema at each time point was determined by comparison with paw volume measured pre-injection. Inhibition of edema was calculated by comparison with vehicle control at the same time point.

EXAMPLE 7

Collagen Induced Arthritis

Groups of 5 BALB/c mice weighing 25±2 g were used for this study. A 4 mg/mouse combination of 4 monoclonal antibodies (mAbs) against type II collagen (D8, F10, DI-2G, and A2; IBL Co., Japan) was administered to mice intravenously on day 0 of the study to induce an inflammatory reaction mimicking rheumatoid arthritis. On day 3 of the study, mice were given LPS (25 mg/mouse) intravenously to potentiate the inflammatory effect. One hour after LPS administration, mice were dosed orally with chicory extract (200 mg/kg), indomethacin (3 mg/kg; Sigma, St. Louis, Mo.), or vehicle control (1% carboxymethylcellulose, CMC; Sigma, St. Louis, Mo.). Mice were dosed with chicory extract or vehicle for two more consecutive days. Volumes of both hind paws were measured using a plethysmometer on days 0, 5, 7, 10, 14, and 17. The increase in paw edema at each time point was determined by comparison with paw volume measured on day 0. Inhibition of edema was calculated by comparison with vehicle control at the same time point. This study was a GLP study (#1038342) performed by MDS Pharma Services (Taiwan).

Statistical Analysis

Data represent means±SE and were analyzed using the Student's t-test or ANOVA. Treatments were considered significantly different if $p<0.001$ for gene expression data and $p<0.05$ for the Griess assay and animal data.

RESULTS

Pro-Inflammatory Gene Expression

Figure 2:
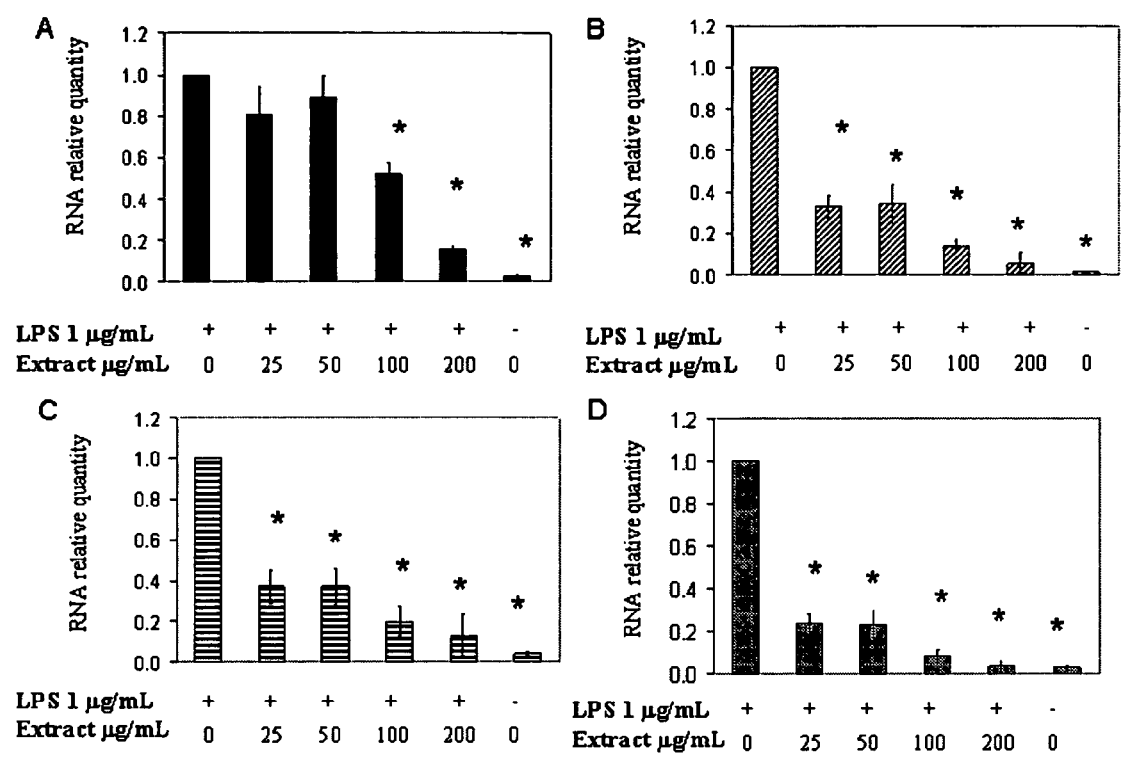
FIG. 2 Effect of chicory extract on pro-inflammatory gene expression in RAW 264.7 murine macrophages. (A) represents cycloxygenase-2 (COX-2) expression; (B) nitric oxide synthase (iNOS); (C) tumor necrosis factor-alpha (TNF-α); (D) interleukin 1, beta (IL1β). Analysis of expression was done using real time PCR techniques. Bars represent the average of 5 analyses±SE. Asterisks indicate values that are significantly different (ANOVA) from the control at p<0.001.

The expression of COX-2, iNOS, TNF-α and IL1β was significantly decreased after LPS-induced macrophages were treated with different concentrations of chicory extract for 6 hours (FIG. 2). The response was dose-dependent with significant activity ($p<0.001$) at 25 µg/mL for iNOS, TNF-α, and IL1β and 100 µg/mL in COX-2. There was no inhibitory effect on the expression of non-inducible COX-1 (data not shown). There was also no evidence of cytotoxicity as measured by the MTT assay in the extract dose range from 0-200 µg/mL after 24 hours of treatment (data not shown).

Griess Assay

Nitric oxide production by RAW macrophages induced with LPS and treated with aspirin or chicory extracts indirectly was measured by the Griess assay. Production of nitric oxide from macrophages was significantly ($p<0.05$) reduced in LPS-induced macrophages treated with different concentrations of chicory extract for 24 hours, as shown in Table 1. The 25 µg/mL treatment had similar inhibitory effect as 10 mM aspirin. There was no evidence of significant cytotoxicity as measured by the MTT assay (data not shown).

TABLE 1

Griess assay

|  | % LPS control | SE |
| --- | --- | --- |
| LPS | 100% | 1.05 |
| DMSO | 42% | 0.40 |
| aspirin 10 µM | 69% | 0.60 |
| chicory 25 µg/mL | 69% | 1.00 |
| chicory 50 µg/mL | 46% | 0.40 |
| chicory 75 µg/mL | 39% | 2.00 |

Rat Paw Edema

Effect of chicory extract of the present invention administered 1 hour after carrageenan injection on rat paw edema. When rats were gavaged with chicory extract (50 or 100 mg/kg) 1 hours after injection of carrageenan in the hind paw, inflammation was reduced for 24 hours, as shown in Table 2. The 50 mg/kg dose reduced inflammation 30%, 37%, and 57% of control at 3 hours, 5 hours, and 24 hours, respectively, with significant differences at 3 hours and 24 hours ($p<0.05$). The 100 mg/kg dose reduced inflammation 40%, 57%, and 76% of control at 3 hours, 5 hours, and 24 hours, respectively with significant results at 3 hours and 24 hours ($p<0.05$). These effects were very similar to the indomethacin (15 mg/kg) treatment, indicating a considerable anti-inflammatory effect.

TABLE 2

Rat Paw Edema

|  | indomethacin | SE | chicory 50 mg/kg | SE | chicory 100 mg/kg | SE |
| --- | --- | --- | --- | --- | --- | --- |
| 3 h | 43% | 8 | 30% | 7 | 40% | 8 |
| 5 h | 36% | 14 | 37% | 13 | 57% | 7 |
| 24 h | 51% | 10 | 58% | 12 | 76% | 11 |

Collagen Induced Arthritis

Effect of chicory extract on inflammation caused by type II collagen monoclonal antibody induced arthritis with LPS challenge. In the collagen induced arthritis model, chicory extract (200 mg/kg) significantly reduced inflammation early in the study but did not maintain significant activity past day 7, as shown in Table 3. Mice were dosed with chicory extract days 3-5 and paw size was measured alternate days beginning on day 5. On day 5, chicory extract reduced inflammation 71% (p=0.002) more than the vehicle control (Table 3). On day 7, chicory extract was still effective, reducing paw size 31% (p=0.02) more than control. On day 10, there was a small but statistically insignificant inhibitory effect, 16% (p=0.09) greater than control. In contrast, indomethacin (3 mg/kg) significantly reduced inflammation days 5-17 (p<0.05).

TABLE 3

Mouse arthritis % inhibition of edema

| day | indomethacin | SE | chicory 200 mg/kg | SE |
|---|---|---|---|---|
| 5 | 83% | 4 | 71% | 15 |
| 7 | 81% | 3 | 31% | 10 |
| 10 | 82% | 6 | 16% | 8 |
| 14 | 77% | 6 | 3% | 15 |
| 17 | 85% | 3 | −6% | 10 |

The sesquiterpene-enriched Chicory extract of the present invention significantly reduces the expression of genes coding for pro-inflammatory proteins in RAW macrophages induced with LPS (FIG. 2). The experiments have shown a dose-dependent down-regulation of COX-2, iNOS, IL1β and TNF-α gene expression (Table 4). All of these genes have a binding site in their promoter region for NF-κB. Therefore, the effect on inflammatory genes may have been mediated through NF-κB. When macrophages were treated with chicory extracts, there was also a dose-dependant decrease in nitric oxide production (Table 1), consistent with down-regulation of inducible inflammatory pathways. It is also demonstrated that COX-1, which is constitutively expressed in most cells, was not affected after treatment with chicory extract (data not shown). This data suggests that chicory extract acts solely on inducible inflammation syndromes.

In order to demonstrate the therapeutic effect of the sesquiterpene-enriched chicory extract, its effects in vivo were investigated. Acute and chronic inflammation inhibitory activities were performed using the rat paw edema and the collagen induced arthritis animal models. In the rat paw edema assay, chicory extract reduced inflammation for 24 hours after carrageenan injection into the hind paw (Table 2). The chicory treatments worked quickly, reducing inflammation by 30% and 40% (at 50 and 100 mg/kg, respectively) 3 hours after carrageenan injection or 2 hours after oral administration. These data indicate that the sesquiterpene-enriched chicory extract preparation was quickly absorbed and biologically available. In addition, chicory extract had a prolonged pharmacological activity. By 24 hours, the 100 mg/kg chicory treatment was still active with an even larger anti-inflammatory effect than was observed at 3 hours, reducing inflammation by 76%. Both 50 and 100 mg/kg treatments had anti-inflammatory activity comparable to the positive control, indomethacin (3 mg/kg). These data illustrate that chicory sesquiterpene lactone enriched extract are effective in reducing certain types of inflammation.

In the collagen induced arthritis model, the sesquiterpene-enriched chicory extract significantly reduced inflammation compared to the control on days 5 and 7 but failed to have an effect thereafter (Table 3). In this study, treatments with extract were discontinued after day 5. Inflammation was controlled while the extract was being administered and for 48 hours thereafter. While not bound by theory, one explanation for this effect is that the extract may be quickly metabolized and does not remain in the body for more than 48 hours in mice. There may be other more complex explanations based on bioavailability, metabolism, pharmacokinetics and in vivo mode of action. The collagen induced arthritis model is similar to the rheumatoid arthritis (RA), which is a complex, multi-factorial, systemic inflammatory disease. Secretion of TNF-α and IL1β into the synovial cavity has been associated with the disease, leading to cartilage loss and bone erosion. Chicory extract was effective in reducing TNF-α and IL1β in vitro, which could explain the reduction in inflammation seen in this study (Table 4).

Overall, the findings in this study indicate that chicory root sesquiterpene lactone extract effectively reduces the expression of pro-inflammatory genes and reduces the production of nitric oxide by macrophages in vitro. Rat and mice studies show that this extract is biologically available and pharmacologically active in vivo, reducing inflammation in two models.

It is to be understood that the above-described embodiments are illustrative of only a few of the many possible specific embodiments, which can represent applications of the principles of the invention. Numerous and varied other arrangements can be readily devised in accordance with

TABLE 4

| Gene (accession number) | Forward | Reverse |
|---|---|---|
| COX-2 (NM_011198) | 5'-TGGTGCCTGGTCTGATGATG-3' | 5'-GTGGTAACCGCTCAGGTGTTG-3' |
| iNos2 (XM_147149) | 5'-CCCTCCTGATCTTGTGTTGGA-3 | 5'-TCAACCCGAGCTCCTGGAA-3' |
| IL1β (NM_008361) | 5'-CAACCA ACAAGTGATATTCTCCATG-3' | 5'-GATCCACACTCTCCA GCTGCA-3' |
| TNF-α (NM_013693) | 5'-CATCTTCTCAAAATTCGAGTGACAA-3' | 5'-TGGGAGTAGACAAGGTACAACCC-3' |
| Actin (NM_007393) | 5'-AACCGTGAAAAGATGACCCAGAT-3' | 5'-CACAGCCTGGATGGCTACGT-3' | these principles by those skilled in the art without departing from the spirit and scope of the invention.

What is claimed is:

1. A method of obtaining a pharmaceutical, nutraceutical, functional food or cosmetic product comprising a chicory extract comprising the steps of:
   i) performing an initial extraction of chicory in a polar solvent to form an extract;
   ii) defatting the extract with a non-polar solvent;
   iii) performing a second extraction of the defatted extract with a third solvent, wherein the third solvent is selected from the group consisting of ethyl acetate, isopropanol, n-propanol, n-butanol, dichloromethane, acetonitrile, and mixtures thereof, resulting in an extract containing sesquiterpene lactones; and iv) removing the solvents from the extract.

2. The method of claim 1 further comprising after step iv), the step of:
   admixing suitable excipients and/or carriers with said extract.

3. The method of claim 1 wherein the polar solvent is ethanol or methanol.

4. The method of preparing a chicory extract of claim 1 wherein the non-polar solvent is selected from the group consisting of n-heptane, pentane, hexane and mixtures thereof.

5. The method of preparing a chicory extract of claim 1 wherein the second extraction is performed with ethyl acetate.

6. The method of preparing a chicory extract of claim 1 wherein the initial extraction is performed at ambient temperature.

7. The method of preparing a chicory extract of claim 1 wherein in step i) the chicory is dry milled roots.

8. The method of preparing a chicory extract of claim 1 wherein the initial extraction and the second extraction are performed for a period of time that result in an extract containing at least 30% sesquiterpene lactones.

9. The method of preparing a chicory extract of claim 1 wherein steps ii) and iii) are performed using counter-current chromatography.

10. A method of treating inflammation in a subject comprising administering to the subject an effective amount of a composition of sesquiterpene-enriched chicory extract wherein the extract is prepared by a method comprising the steps of:
   i) performing an initial extraction of chicory in a polar solvent to form an extract;
   ii) defatting the extract with a non-polar solvent;
   iii) performing a second extraction of the defatted extract with a third solvent, wherein the third solvent is selected from the group consisting of ethyl acetate, isopropanol, n-propanol, n-butanol, dichloromethane, acetonitrile, and mixtures thereof, resulting in an extract containing sesquiterpene lactones; and
   iv) removing the solvents from the extract.

11. The method of treating inflammation of claim 10 wherein the administering to the subject is performed orally or topically.

12. The method of treating inflammation of claim 10 wherein the extract contains at least 60% sesquiterpene lactones.

13. A pharmaceutical, nutraceutical, functional food or cosmetic for the treatment of inflammation comprising a sesquiterpene lactone enriched chicory extract, wherein the extract is prepared by a method comprising the steps of:
   i) performing an initial extraction of chicory in a polar solvent to form an extract;
   ii) defatting the extract with a non-polar solvent;
   iii) performing a second extraction of the defatted extract with a third solvent, wherein the third solvent is selected from the group consisting of ethyl acetate, isopropanol, n-propanol, n-butanol, dichloromethane, acetonitrile, and mixtures thereof, resulting in an extract containing sesquiterpene lactones; and
   iv) removing the solvents from the extract.

14. The composition of claim 13 wherein the extract contains at least 60% sesquiterpene lactones.

15. A method for treating inflammatory or autoimmune diseases in a mammal, said method comprising administering to the mammal a therapeutically effective amount of a sesquiterpene-enriched chicory extract, wherein the extract is prepared by:
   i) performing an initial extraction of chicory in a polar solvent to form an extract;
   ii) defatting the extract with a non-polar solvent;
   iii) performing a second extraction of the defatted extract with a third solvent resulting in an extract containing sesquiterpene lactones; and
   iv) removing the solvents from the extract.

16. The method of claim 15 wherein the inflammation or autoimmune disease is caused by a disease selected from rheumatoid arthritis, asthma, inflammatory bowel disease, Crohn's disease, multiple sclerosis, psoriasis and skin rushes, chronic obstructive pulmonary disease, allergic rhinitis, cardiovascular disease, lupus, and metabolic syndrome.

17. The method of claim 15 wherein the mammal is a human.

18. The method of treating inflammation of claim 15 wherein the administering to the mammal is performed orally or topically.

* * * * *